US00PP10162P

United States Patent [19]

Gross

[11] Patent Number: Plant 10,162

[45] Date of Patent: Dec. 23, 1997

[54] POINSETTIA PLANT 'RED BARON'

[75] Inventor: Eduard Gross, Nanteuillet, France

[73] Assignee: Paul Ecke Ranch, Inc., Encinitas, Calif.

[21] Appl. No.: 630,896

[22] Filed: Apr. 4, 1996

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 3,219 6/1972 Jacobsen ..... Plt./86.4
P.P. 6,592 2/1989 Gross ..... Plt./86.4

OTHER PUBLICATIONS

Lipov–ROM citation of 'Red Baron' DK PBR16794, Oct. 15, 1995.

*Primary Examiner*—James R. Feyrer
*Attorney, Agent, or Firm*—Arnold, White & Durkee

[57] ABSTRACT

Poinsettia 'Red Baron' is a new cultivar, distinguished by thick glossy dark red flower bracts, strong stems and self-branching characteristics. 'Red Baron' is a sport of the red bracted 'Supjibi' (U.S. Plant Pat. No. 6,592) with the same flowering response and cultural requirements. The new plant produces a very desirable branched flowering pot plant. The new plant is resistant to epinasty after being confined to shipping containers. The post-production foliage and bract retention are good.

2 Drawing Sheets

BACKGROUND OF THE NEW PLANT

Poinsettia 'Red Baron' is the subject of an application for Plant Breeders rights protection filed in Denmark on Oct. 15, 1995 as PBR application number 16794. The same plant is also the subject of an application for protection in the European community filed on Aug. 30, 1995 as EC 95-2063.

The new poinsettia cultivar originated as a sport of 'Supjibi' (U.S. Plant Pat. No. 6,592) in my greenhouse in Blanzac, France in 1993. It was selected, because of its thick glossy maroon red flower bracts. The bract color is the darkest red of all known poinsettias. The glossy or "waxy" bract surface is unique, distinguishing it from other poinsettia cultivars, and seemed to make it a desirable plant for commercial greenhouse production. After selection, 'Red Baron' was vegetatively reproduced form stem cuttings for test purposes in Encinitas, Calif. By subjecting clones of this plant to successive generations of vegetative propagation, it was demonstrated that the distinctive characteristics of 'Red Baron' held true from generation to generation. Grown under the same greenhouse environment, 'Red Baron' had the same growth habit and flowering response time as the parent plant 'Supjibi'. The flower bracts are relatively narrower than those of Supjibi.

DESCRIPTION OF THE PHOTOGRAPHS

Poinsettia 'Red Baron' is illustrated in the accompanying color photographs. Sheet 1 is a top view of the plant showing flower bract formation. The plant shown has not reached full maturity. The bract color is somewhat deeper in red color than the true bract color which is more accurately depicted in the drawing of Sheet 2.

Sheet 2 is a side view of the mature plant in full flower. The true color of the bracts is more closely depicted in this photograph. One of the unique traits of 'Red Baron' is the very waxy, shiny bract surface. The waxy surface causes a reflection that makes it difficult to photograph the true color.

DESCRIPTION OF THE PLANT

The following is a detailed description of this new poinsettia as observed in Encinitas, Calif. USA during December 1994. Observations were recorded from flowering plants, grown as one branched plant per pot. The pot was 14 cm in diameter and 11 cm in height. Color designations are compared to the 1986 edition of R.H.S. Color Chart, first published in 1966 by The Royal Horticultural Society, London, England.

The Plant

Origin: Sport of 'Supjibi' (U.S. Plant Pat. No. 6,592).

Classification:

*Botanical.*—*Euphorbia pulcherrima* Willd.

*Common name.*—Poinsettia.

*Cultivar name.*—'Red Baron'.

Form: Shrub.

Height: Short — Medium.

Growth habit: As a single stemmed plant, upright and vigorous with self-branching side shoots. The application of a chemical growth retardant may not be needed to restrict height for commercial pot plant production. I observed one branched plant in a pot with an overall height of 38 cm and an overall width of 45 cm. The bract diameter of individual flowers was 25 cm.

Branching: Axillary branches will develop and terminate in a flower without pinching. However, it is usually desirable to pinch 'Red Baron' before induction and remove all terminal dominance. Then, all axillary branches will develop uniformly and at a faster rate.

Growth rate: Rooting of stem cutting occurs in 12–18 days under intermittent mist.

Flowering: The plant will flower in eight to nine weeks under continuous long night conditions and night temperatures of 16–18 degrees C. Like its parent, ('Supjibi'), 'Red Baron' will be in full bloom in late November in the northern hemisphere under natural daylength conditions.

Foliage: The foliage was clean and uniformly dark green from bottom to top of the plant. The leaves were of medium size, leaf blades typically being 13–14 cm long and 8–9 cm wide with leaf petioles 4–6 cm long. The upper and under surfaces of the leaf petiole are red.

*Leaf shape.*—Typical leaves are ovate with obtuse to acute bases and acuminate tips. Leaf margins are mostly entire. An occasional lower leaf is modestly lobed on either side of the leaf blade.

*Leaf surface.*—The upper surface is glabrous and the under surface is slightly pubescent.

*Color.*—Upper side — Green, near R.H.S. 147A.

*Retention.*—The foliage retention is good even under low light intensities in the consumer's home.

Bracts: Generally there were 15–17 glossy red bracts of various sizes subtending the cyathia. The primary bracts had blades typically 13–14 cm long and 7–8 cm wide with petioles 4 cm long.

*Shape.*—Primary bracts are ovate with acute bases and acuminate tips. Leaf margins are entire or weakly lobed with 1 small indentation on either side of the bract. Secondary bracts are ovate to elliptic and have entire margins.

*Surface.*—The bract surface is shiny and waxy.

*Color.*—Upper side — Maroon, darker than R.H.S. 45A. Under side — Maroon, near R.H.S. 45A.

Flowers: Generally, 13–14 cyathia (flowers) were present when the plant was in full bloom. Each cyathium is about 7 mm long and 7 mm wide, green in color, and fringed maroon at the distal end. One or two orange nectar cups protrude from the side of each cyathium. The flower pedicel is also green and about 6 mm in length. The stamens protruding from the cyathia are maroon. The stigmas are maroon and trifurcate. The pollen is yellow and copious. Cyathia retention was about three weeks beyond the time the flower was fully mature.

*Nectar exudate.*—Present, abundant.

*Seed formation.*—Self-incompatible.

*Fertility.*—Not observed.

Post production: 'Red Baron' was resistant to epinasty after being confined to shipping containers. The foliage and bract retention were good.

What is claimed is

1. A new and distinct variety of Poinsettia plant, substantially as herein shown and described, distinguished by its strong stems, thick waxy dark red flower bracts, self branching and good leaf and bract retention in the consumer environment.

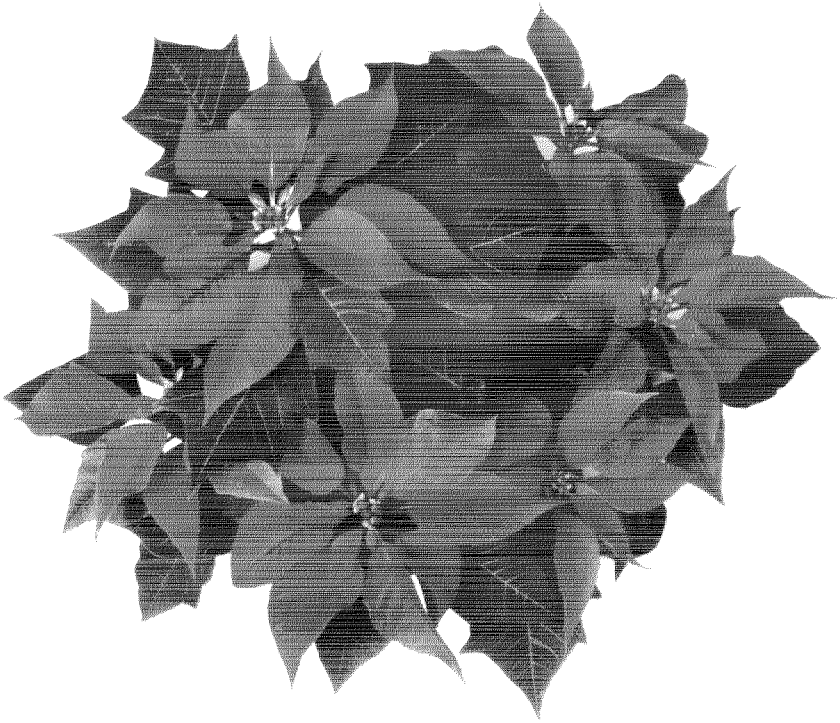

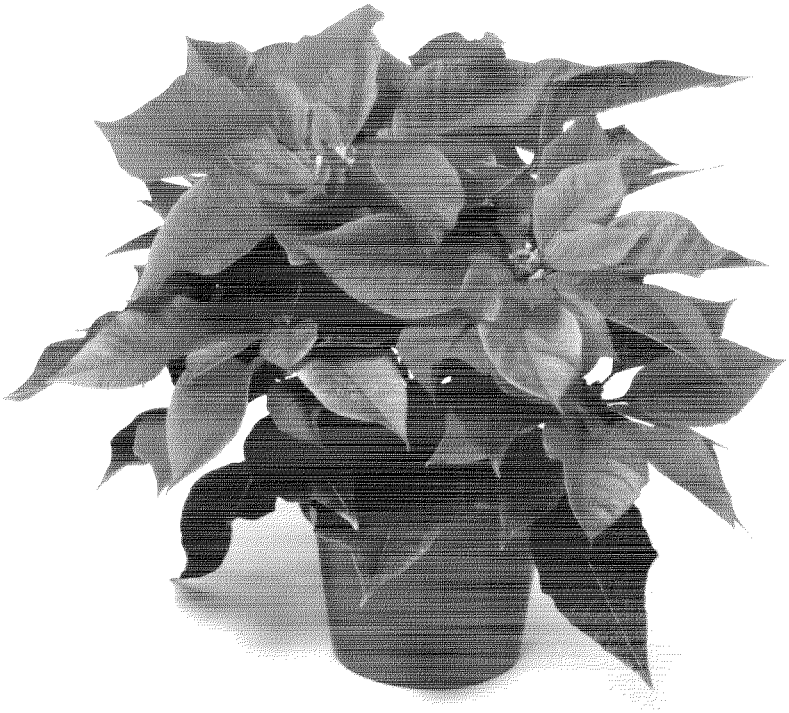

* * * * *